US00PP36274P2

(12) United States Plant Patent
Jachertz

(10) Patent No.: US PP36,274 P2
(45) Date of Patent: Nov. 26, 2024

(54) ***GASTERALOE* PLANT NAMED 'BINL-19145'**

(50) Latin Name: ***Gasteraloe carinata* var. *verrucosa* x *aristata***
Varietal Denomination: BINL-19145

(71) Applicant: Botanical Innovation, BV, Wageningen (NL)

(72) Inventor: Christian Jachertz, Amposta (ES)

(73) Assignee: Botanical Innovation B.V. (NL)

( * ) Notice: Subject to any disclaimer, the term of this patent is extended or adjusted under 35 U.S.C. 154(b) by 0 days.

(21) Appl. No.: 18/387,399

(22) Filed: Nov. 6, 2023

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct cultivar of *Gasteraloe* plant named 'BINL-19145' is disclosed, characterized by open, slightly upright rosettes with dark green leaves, and elevated dark green lenticel dots. The new variety is a *Gasteraloe*, typically used as an ornamental plant.

3 Drawing Sheets

Latin name of the genus and species: *Gasteraloe carinata* var. *verrucosa* x *aristata*.

Variety denomination: 'BINL-19145'.

BACKGROUND OF THE INVENTION

The new cultivar is a product of a planned breeding program to produce distinct and better performing *Gasteraloe* varieties. The new variety was selected as a seedling resulting from the crossing made by the inventor, Christian Jachertz, a citizen of Spain, in 2017. The seed parent is the unpatented *Gasteria carinata* var. *verrucosa* '#1080', a variety from the inventor's breeding line. The pollen parent is the unpatented *Aloe aristata* '#2054', also from the inventor's breeding line. The new variety was selected by the inventor in 2018 at a commercial greenhouse Amposta, Spain.

Asexual reproduction of the new cultivar 'BINL-19145' by terminal cuttings was first performed in Amposta, Spain at a commercial greenhouse in March 2019, and has shown that the unique features of this cultivar are stable and reproduced true to type through successive generations.

SUMMARY OF THE INVENTION

The cultivar 'BINL-19145' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BINL-19145'. These characteristics in combination distinguish 'BINL-19145' as a new and distinct *Gasteraloe* cultivar:

1. Dark green leaves with slightly elevated dark green lenticel dots.
2. Open and slightly upright rosette-shaped plant.

PARENT COMPARISONS

Plants of the new cultivar 'BINL-19145' are similar to plants of the female parent in most horticultural characteristics, however, plants of the new cultivar 'BINL-19145' differ-in the following characteristics:

1. Leaf color of the new variety is dark green with dark green lenticel dots, while the leaf color of the seed parent is dark green with white lenticel dots.
2. Plants of the new variety have a rosette shape, while plants of the seed parent have in line growing leaves.
3. Leaves of the new variety are shorter than leaves of the seed parent.
4. Plants of the new variety are faster growing than plants of the seed parent.

Plants of the new cultivar 'BINL-19145' are similar to plants of the male parent in most horticultural characteristics, however, plants of the new cultivar 'BINL-19145' differ in the following characteristics:

1. Leaf color of the new variety is dark green with dark green lenticel dots, while the leaf color of the pollen parent is light green with white lenticel dots.
2. Plants of the new variety have an open rosette shape, while plants of the pollen parent have a full rosette shape with many more densely growing leaves.

COMMERCIAL COMPARISONS

Plants of the new cultivar 'BINL-19145' are similar to plants of the commercial variety *Gasteraloe* 'D Delta', U.S. Plant Pat. No. 30,905. However, plants of the new cultivar differ in the following characteristics:

1. Leaf color of the new variety is dark green with dark green lenticel dots, while the leaf color of this comparator is dark green with white lenticel dots.

Plants of the new cultivar 'BINL-19145' are similar to plants of the commercial variety *Gasteria* 'Royal Wolfgang', U.S. Plant Pat. No. 25,667. However, plants of the new cultivar differ in the following characteristics:

1. Leaf color of the new variety is dark green with dark green lenticel dots, while the leaf color of this comparator is dark green with white lenticel dots.

Plants of the new cultivar 'BINL-19145' are similar to plants of the commercial variety *Gasteria* 'WT-01', U.S. Plant Pat. No. 22,012. However, plants of the new cultivar differ in the following characteristics:

1. Leaf color of the new variety is dark green with dark green lenticel dots, while the leaf color of this comparator is dark green with white lenticel dots.

BRIEF DESCRIPTION OF THE PHOTOGRAPHS

The accompanying photograph in FIG. 1 illustrates in full color a typical plant of 'BINL-19145' grown in a greenhouse. The plant is approximately 40 weeks of age.

Figure 1:
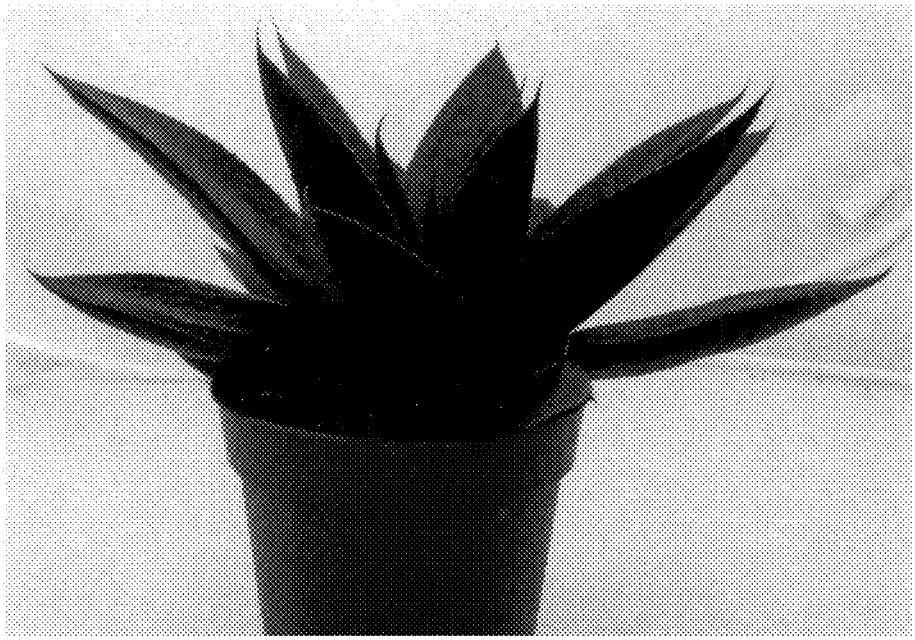
Figure 2:
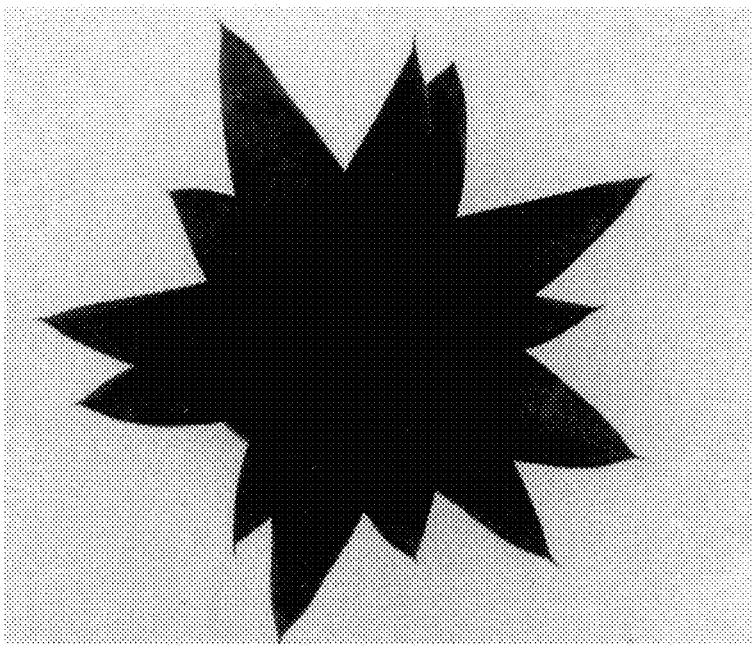
FIG. 2 is a top view of the same plant.
Figure 3:
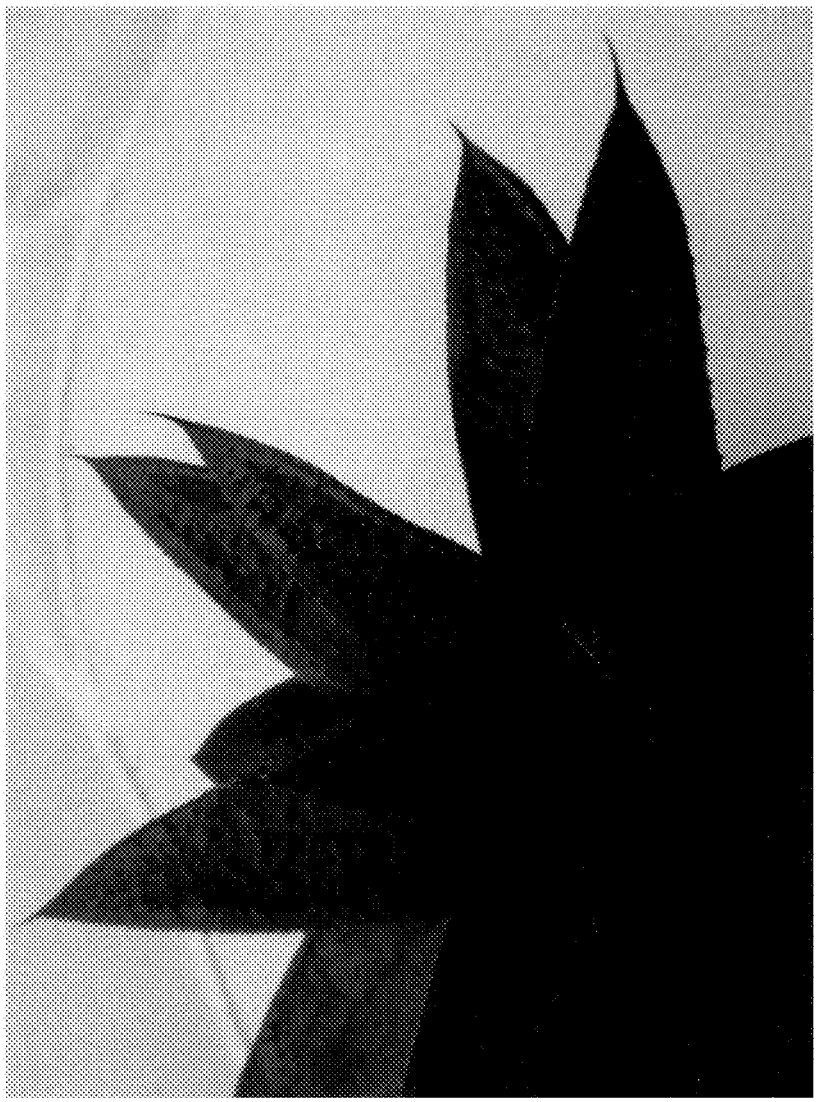
FIG. 3 is a close-up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'BINL-19145' plants at 40 weeks of age, grown in a greenhouse in Amposta, Spain during August. The growing temperature ranged from 15° C. to 18° C. at night to 18° C. to 20° C. during the day. Measurements and numerical values represent averages of typical flowering types.

Botanical classification: *Gasteraloe* 'BINL-19145'.

PROPAGATION

Time to initiate roots: About 14 days at approximately 20° C. in summer or winter.

Time to produce rooted cutting: About 80 days at 20° C. in summer; 90 days at 20° C. in winter.

Description of roots: Fibrous, thick, moderately dense, freely branching. Young roots are white, older roots are brown in color, not accurately measured with R.H.S. chart.

PLANT

Plant type: Perennial potted plant.

Plant shape: Broad obovate to near orbicular.

Growth habit: Basal rosette of leaves.

Plant spread: Average 11.2 cm.

Height: Average 8.8 cm.

Growth rate: Low to moderate.

Plant vigor: Low to moderate.

Age of plant described: Approximately 40 weeks.

Branching habit: Leaves in basal rosettes.

Pinching: Pinching not required.

Number of primary (main) branches per plant: Average 1 basal rosette.

Number of secondary (lateral) branches per plant: None.

FOLIAGE

Leaf:

*Arrangement.*—Single rosette.

*Quantity.*—Average 24 per rosette.

*Average length.*—7.1 cm.

*Average width.*—2 cm.

*Shape.*—Narrow ovate to lanceolate, succulent.

*Aspect.*—Slightly concave to nearly flat.

*Apex.*—Long acuminate with a soft mucronate tip.

*Base.*—Broad cuneate.

*Margin.*—Finely pustulate-dentate, average length of teeth: 0.3 mm, average width of teeth: 0.5 mm, colored RHS Green NN137A.

*Texture.*—Top surface: Densely pustulate, randomly placed on lamina, average diameter: 0.1 cm, average height: less than 0.2 mm, colored RHS Green NN137A and Yellow-Green 147A. Bottom surface: Densely pustulate, randomly placed on lamina and a central ridge, average diameter: 0.1 cm, average height: 0.2 mm and less, colored RHS Green NN137A and Yellow-Green 147A.

*Pubescence.*—None.

*Luster, upper side.*—Glossy.

*Luster, under side.*—Glossy.

*Rugosity, upper side.*—Non-rugose.

*Rugosity, under side.*—Non-rugose.

*Color.*—Young foliage upper side: RHS Green 137A, fading to Yellow-Green 144A to 148D towards the base. Young foliage under side: RHS Green 137A, fading to Yellow-Green 144A to 152D towards the base. Mature foliage upper side: A blend of RHS Green NN137A and Yellow-Green 147A, fading to Yellow-Green 143A and 144A towards the base. Mature foliage under side: RHS Yellow-Green 147A fading to 143B towards the base.

*Venation.*—Pattern: Parallel. Venation color upper side: A blend of RHS Green NN137A and Yellow-Green 147A, fading to Yellow-Green 143A and 144A towards the base. Venation color under side: RHS Yellow-Green 147A, fading to Yellow-Green 143B towards the base.

OTHER CHARACTERISTICS

Flowers: Not observed to date.

Seeds and fruits: None observed to date.

Disease/pest resistance: Similar resistance nor susceptibility to normal diseases and pests of *Gasteraloe* has been observed.

Temperature tolerance: Tolerates temperatures up to 40° C. Hardy to USDA zones 10 to 12. Low tolerance to rain. High tolerance to wind.

What is claimed is:

1. A new and distinct cultivar of *Gasteraloe* plant named 'BINL-19145' as herein illustrated and described.

* * * * *